United States Patent
Büchi et al.

[11] 3,963,783
[45] June 15, 1976

[54] 4-METHYL-8-VINYL-4,7- AND -4,8-NONADIENALS

[75] Inventors: George Hermann Büchi; Hans Wüest, both of Mattapan, Mass.; Günther Ohloff, Bernex, Geneva; Hugo Strickler, Onex, Geneva, both of Switzerland

[73] Assignee: Firmenich S.A., Geneva, Switzerland

[22] Filed: June 12, 1968

[21] Appl. No.: 736,267

[30] Foreign Application Priority Data
June 15, 1967 Switzerland............ 8529/67
Dec. 14, 1967 Switzerland............ 17568/67

[52] U.S. Cl.............. 260/601 R; 252/522; 260/604 R; 260/632 B
[51] Int. Cl.².................. C07C 47/20
[58] Field of Search............ 260/601, 601 R

[56] References Cited
UNITED STATES PATENTS
3,574,715  4/1971  Marbet et al. ........... 260/601 R OTHER PUBLICATIONS
Swern, Organic Reactions, vol. 7, 1953, pp. 385, 388 and 399.
Braun et al., Ber., "Deutch Chemistre Gesel.", vol. 67, p. 1735 (1934).
Crandall et al., Journ. of Org. Chem., vol. 32, pp. 435–439, 1967.
Cresson et al., Compte Rend. Acad. Sci., vol. 262, Ser. C., pp. 1157–1160, 1966.
Julia et al., Bull. Soc. Chim., Ser. 5, No. 10, Oct. 1962, pp. 1947–1952.
Rosowsky, A., in Heterocyclic Compounds, Part I, 1964, pp. 1, 31, 40–43, 349–352.

Primary Examiner—Paul M. Coughlan, Jr.
Assistant Examiner—D. B. Springer
Attorney, Agent, or Firm—Pennie & Edmonds

[57] ABSTRACT

The present invention relates to a novel process for preparing unsaturated aldehydes comprising four double bonds of formula

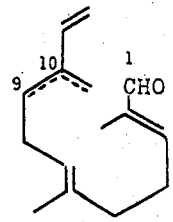

I a, b wherein one of the double bonds is represented by the dotted lines. Aldehyde I$a$ (called α-sinensal) corresponds to the above formula wherein the double bond represented by the dotted lines is in the main carbon chain. Aldehyde I$b$ (called β-sinensal) corresponds to the above formula wherein the double bond represented by the dotted lines is in the side chain. The invention also relates to new intermediates used in the said new process and to methods for preparing them. The said intermediates have also valuable organoleptic properties and are useful as fragrances in the preparation of perfumes, perfumed products and artificial essential oils.

3 Claims, No Drawings

4-METHYL-8-VINYL-4,7- AND -4,8-NONADIENALS

BACKGROUND OF THE INVENTION

I. Field of the Invention

This invention relates to the preparation of unsaturated aldehydes and specifically, to the preparation of the α- and β-sinensals.

II. Description of the Prior Art

The α-and β-sinensals are sesquiterpenic aldehydes which have been discovered in the oil of China orange (Citrus sinensis) [see J. Org. Chem. 30, 1690 (1965); Tetrahedron Letters 295 (1966)] and which owing to their organoleptic properties have a great value as flavouring agents for foods and beverages.

For the α-sinensal (Ia) and β-sinensal (Ib) whose structure is derived from ocimene cis or trans and from myrcene (see formulae hereafter), the denomination α and β, respectively, has been adopted from analogy with the α-and β-farnesenes. In the past, a reverse system has been used, α in place of β and vice versa (see for instance the above references).

Until now the α-and β-sinensals have not been prepared synthetically.

SUMMARY OF THE INVENTION

It has now been discovered that the α- and β-sinensals can be prepared from simple and readily available starting materials.

The process according to the invention comprises condensing 4-methyl-8-vinyl-4,7-nonadienal (IIa) or 4-methyl-8-vinyl-4,8-nonadienal (IIb) with an N-substituted propionalimine the substituent of which is a member selected from the group consisting of linear and branched aliphatic and alicyclic radicals having from 2 to 8 carbon atoms, in the presence of a mixed metallating agent and subsequently hydrolysing the condensation product in an at least partly aqueous acidic medium.

DESCRIPTION OF THE PREFERRED EMBODIMENTS

For the condensation of the dienals IIa and IIb with the N-substituted propionalimine mmixed metallating agents consisting for instance of the reaction product of an alkali metal, an alkyl halide and a secondary amine can be used. Alkali metals such as sodium potassium or lithium or alloys thereof can be used. Alkyl halides having one to 6 carbon atoms such as methyl iodide, ethyl iodide or bromide, n-propyl bromide or iodide, isopropyl bromide or iodide, butyl chloride or bromide, amyl bromide, isobutyl iodide, hexyl chloride, bromide or iodide can be used. Secondary amines such as diethylamine, diisopropylamine, piperidine, dicyclohexylamine, piperazine, dibutylamine, diisobutylamine and ethyl-tert.-butylamine can be used. A preferred mixed metallating agent consists of the reaction product of lithium metal, methyl iodide and diisopropylamine.

The N-substituted propionalimine used in the process of the invention can be N-ethyl, N-cyclohexyl-, N-methylcyclohexyl-, N-tert.-butyl-, N-propyl-, N-isopropyl-, N-isobutyl-, N-sec.-butyl-, N-amyl- or N-neopentyl-propionalimine. A preferred group of such imines includes N-cyclohexyl- and N-tert.-butyl-propionalimine. The above imines can be prepared according to known methods [see Bull. Soc. Chim. France 14, 708 (1947)].

The condensation according to the invention can be carried out at temperatures comprised between —80° and 0° under an inert atmosphere, preferably in the vicinity of —60° and under nitrogen.

For the hydrolysis of the condensation product aqueous acidic media such as mixtures of mineral or organic acids and at least partly aqueous solvents are used. Acids such as phosphoric, sulphuric, perchloric, hydrochloric, oxalic, acetic, trifluoroacetic, tartaric, malonic and citric acid can be used. Solvents such as water and mixtures of water and a water-miscible organic solvent, e.g. methanol, ethanol, acetone, dioxane, tetrahydrofurane and dimethoxyethane, can be used. A preferred hydrolising medium comprises an aqueous oxalic acid solution.

According to the invention, the aldehydes IIa and IIb can be prepared by epoxidising the non conjugated double bond of ocimene and myrcene, respectively, by means of a peracid in a buffered medium, converting the resulting epoxide into the corresponding secondary alcohol and condensing said alcohol with an unsubstituted vinyl ether in the presence of a condensation agent.

The following scheme summarises the process of the invention for preparing aldehydes IIa and IIb. The dotted lines in the formula below represent one double bond and refer to the ocimene and myrcene structures. Ocimene has the double bond in the main chain, myrcene has the double bond in the side chain. Where substances with ocimene structure are concerned, the configurations shown in the scheme below are trans. However, the same scheme applies also to compounds with an ocimene cis-configuration.

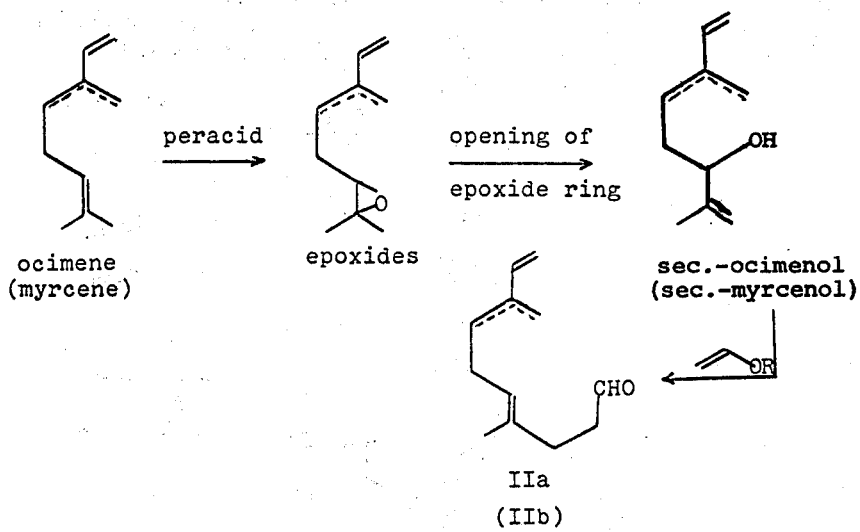

ocimene (myrcene) → epoxides → sec.-ocimenol (sec.-myrcenol) → IIa (IIb)

For the epoxidation, peracids such as peracetic, perbenzoic, mono-chloroperbenzoic and perphthalic acid in chlorinated solvents such as chloroform, methylene choride, trichlorethylene and dichloroethane can be used. Peracetic acid in methylene chloride is a preferred combination of reagent and solvent. Buffering agents such as organic alkali salts can be used in the epoxidation. A group of such salts includes sodium or potassium formate, acetate, propionate, butyrate, oxalate, citrate and tartrate. Sodium acetate is a preferred buffering agent.

The selective epoxidation of the non conjugated double bond of ocimene and myrcene without affecting the other double bonds is critical and must be performed under carefully controlled conditions in order that a good yield of the desired epoxide be obtained. For instance it has been discovered that controlling the reaction temperature in the usual way is not sufficient. In fact, the cooling power of the temperature controlling device (cooling apparatus) must be adjusted so that when the addition of the epoxidising agent has been started at a certain rate, the temperature should soon reach a certain level and stay at this level until the addition of the epoxidising agent is completed. For optimum yields for instance, the reaction vessel should preferably be cooled to about 0° C. and the epoxidising agent added dropwise at such a rate that temperature rises first to 20°–25° and then stays at this level without the cooling device having to be removed.

The secondary alcohols corresponding to ocimene epoxide and myrcene epoxide, respectively, (and called sec.-ocimenol and sec.-myrcenol, respectively, hereinafter) are obtained by opening the epoxide ring. It has been discovered surprisingly that the conditions which are suitable for the conversion of the ocimene epoxide into its corresponding secondary alcohol are not at all favourable for the conversion of the myrcene epoxide into its corresponding secondary alcohol and vice versa. Indeed, in order to obtain the desired secondary alcohols the two conversions should proceed under rather antagonistic conditions since ocimene epoxide must be opened under acidic conditions while myrcene epoxide must be opened under basic conditions. For converting the ocimene epoxide to sec.-ocimenol, diluted aqueous mineral acids or solutions of strong organic or sulphonic acids in organic solvents can be used. Aqueous mineral acids which can be used comprise aqueous solutions of sulphuric, phosphoric, hydrochloric and perchloric acid. Strong organic or sulphonic acid solutions which can be used comprise solutions of trifluoracetic and trichloracetic or benzene-, toluene- or naphthalenesulphonic acids in organic solvents such as aromatic solvents, e.g. toluene or chlorobenzene. For converting ocimene epoxide to sec.-ocimenol aqueous sulphuric acid or benzenic toluene-sulphonic acid solutions are preferably used.

For converting myrcene epoxide to sec.-myrcenol an organo-metallic base such as a metal dialkylamide in a non reactive solvent can be used. Such bases comprise lithium, sodium or potassium diisopropylamide, diisobutylamide or dicyclohexylamide in solvents such as ether, benzene, dioxane or cyclohexane. For converting myrcene epoxide to sec.-myrcenol lithium diisopropylamide in cyclohexane is preferably used.

The condensation of sec.-myrcenol and sec.-ocimenol with an unsubstituted vinyl ether can be performed in the presence of a condensation agent. The condensation agent can be a mixture of a salt of a heavy metal with an alkali metal salt which can act as a stabiliser. The heavy metal can be selected from the group of metals known to form organo-metal complexes, e.g. mercury, silver, lead, copper, iron, palladium, cobalt and magnesium. The above salts should preferably be at least partly soluble in the organic reaction medium, and the acids from which they are derived are preferably organic acids, for instance formic, acetic, propionic or citric acid. A preferred condensation agent is a mixture of mercury and sodium acetates.

Unsubstituted vinyl ethers such as methyl, ethyl, propyl, isopropyl, butyl and other alkyl vinyl ethers can be used in the above condensation. For reasons of availability, ethyl and butyl vinyl ethers are preferred. The condensation can be carried out at widely varying temperatures and using as a solvent an excess of the vinyl ether, under an inert atmosphere. A preferred reaction temperature is the boiling temperature of the vinyl ether used in the condensation.

According to the invention, another method for obtaining aldehyde IIa comprises condensing, by a Wittig-type reaction, levulinaldehyde diethylacetal with 4-methyl-3,5-hexadienylenetriphenylphosphorane and subsequently hydrolysing the condensation product in an acidic aqueous-organic medium.

The phosphorane used in the above Wittig reaction can be obtained according to conventional methods from the corresponding halide (bromide or iodide) via the corresponding phosphonium salt. The following scheme summarises this method for preparing aldehydes IIa

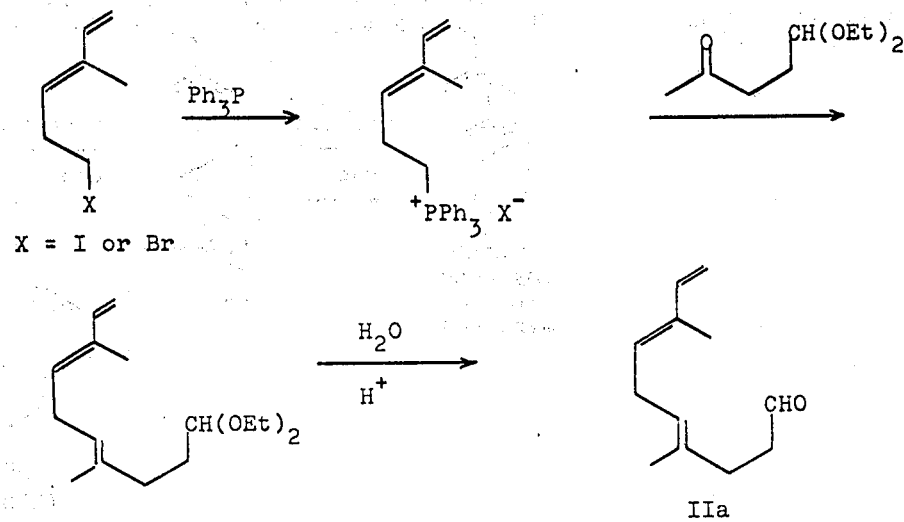

The above Wittig-type condensation can be carried out under the conditions generally used for these reactions, the phosphonium salt being suspended in ether under nitrogen and the phosphorane being generated at 0° by the dropwise addition of a solution of phenyl-lithium in benzene or of an alkyl-lithium such as a butyl- or hexyl-lithium in hexane. When the phosphorane is formed, a solution of the levulinaldehyde acetal is added dropwise and thereafter the reaction product is isolated as usual.

Hydrolysis of the resulting diethylacetal of IIa can be performed in an acidic mixture of water and an organic solvent. Most common strong acids and most watermiscible organic solvents can be used. Acids such as sulphuric, hydrochloric, phosphoric, perchloric benzenesulphonic and trifluoracetic acids and solvents such as tetrahydrofuran, acetone, dimethoxyethane and dioxan can be used. A preferred combination is perchloric acid in aqueous tetrahydrofuran.

According to the invention, another process for obtaining aldehyde IIb comprises condensing a myrcenyl halide of formula

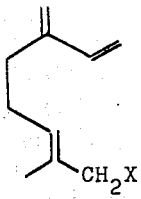

wherein X represents bromine or iodine, with a N-substituted ethanal-imine, the substituent of which is a member selected from the group consisting of linear and branched aliphatic and alicyclic radicals having from 2 to 8 carbon atoms, in the presence of a mixed metallating agent and subsequently hydrolysing the condensation product in an at least partly aqueous acidic medium.

For the condensation of the myrcenyl halide with the N-substituted ethanalimine mixed metallating agents consisting for instance of the reaction product of an alkali metal, an alkyl halide and a secondary amine can be used. Alkali metals such as sodium, potassium or lithium or alloys thereof can be used. Alkyl halides having one to 6 carbon atoms such as methyl iodide, ethyl iodide or bromide, N-propyl bromide or iodide, isopropyl bromide or iodide, butyl chloride, bromide or iodide, amyl bromide, isobutyl iodide, hexyl chloride, bromide or iodide can be used. Secondary amines such as diethylamine, diisopropylamine, piperidine, dicyclohexylamine, piperazine, dibutylamine, diisobutylamine, ethyltert.-butylamine can be used. A preferred mixed metallating agent consists of the reaction product of lithium metal, methyl iodide and diisopropylamine.

The N-substituted ethanalimine used in the process of preparing IIb can be N-ethyl-, N-cyclohexyl-, N-methylcyclohexyl-, N-tert.-butyl-, N-propyl, N-isopropyl-, N-isobutyl-, N-sec.-butyl-, N-amyl- or N-neopentyl-ethanalimine. A preferred group of such imines comprises N-cyclohexyl- and N-tert.-butyl-ethanalimine. The above imines can be prepared according to known methods [see Bull. Soc. Chim. France 14, 708 (1947)].

The myrcenyl halide used in the above condensation can be obtained by means of the usual methods for halogenating alcohols from the corresponding primary myrcenol. This alcohol can result from the $SeO_2$ oxidation of myrcene [Bull. Soc. Chim. France 5, 931 (1938)]. As halogenating agents phosphorus tribromide or trichloride can be used.

The condensation between the myrcenyl halide and the ethanalimine is carried out at temperatures comprised between −60° and 0°, preferably around −20° under nitrogen.

For the hydrolysis of the condensation product aqueous acidic media are used, for instance mixtures of mineral or organic acids with an at least partly aqueous solvent. Acids such as phosphoric, sulphuric, perchloric, hydrochloric, oxalic, acetic, trifluoracetic, tartaric, malonic and citric acids can be used. A preferred hydrolising medium is an aqueous oxalic acid solution.

The aldehydes Ia and Ib, (α-and β-sinensals) although structurally isomeric, do not isomerise spontaneously one to the other under normal conditions. It has now been discovered that β-sinensal can be isomerised to α-sinensal when heated in the presence of a carbon-palladium catalyst. This catalyst can be one of those catalysts used for hydrogenation purposes using gaseous hydrogen. For the above isomerisation the catalyst should preferably be activated by a short contact with gaseous hydrogen. It may also be convenient to use a solvent such as methanol or ethanol for the isomerisation which may be carried out by heating the reagents for a few hours to 48 hours at the boiling temperature of the solvent. After the isomerisation, the α-sinensal can be isolated by fractional distillation.

The mono-epoxides of trans-ocimene and cis-ocimene are fragrant substances having interesting odoriferous properties. They are particularly useful for enhancing and reinforcing the top odour of perfume compositions and are advantageously used in proportions of 0.5 – 3%, based on the total weight of a perfume composition, 1 to 2% being a preferred range. These figures are not absolute limits since the said epoxides can also be used in higher proportions depending on the odoriferous effects to be obtained.

The aldehydes 4-methyl-8-vinyl-4,7-nonadienal (IIa) and 4-methyl-8-vinyl-4,8-nonadienal (IIb) are powerful fragrances. They have similar odoriferous properties and develop floral, incense-like odours having a pine-like note. Both aldehydes are useful for reinforcing the top odour of perfume compositions. IIa and IIb are advantageously used at concentrations of 0.1 to 0.3 %, based on the weight of a perfume composition. However, higher concentrations, e.g. of 1% or more, or concentrations lower than 0.1% can be used depending on the odour effects to be obtained.

The invention is further illustrated by the following Examples in which temperatures are given in centigrade degrees.

Example 1

Preparation of α-sinensal a. Epoxidation of trans-ocimene

A solution of 204 g. of trans-ocimene and 150 g. of sodium acetate in 750 ml. of methylene chloride was stirred for one hour at room temperature, then it was cooled to 0° C. within about 15 min. Then, the addition of a solution of 3 g. of sodium acetate in 315 g. of 42% peracetic acid was started dropwise at a rate adjusted so that the temperature rose to 20°–25°. Without removing the cooling device but by maintaining a suitable rate of addition, the temperature was kept constant until the addition of the peracetic acid was completed. Under these conditions, the addition took one hour. The mixture was stirred for an additional four hours period at room temperature then the solid was removed by filtration and rinsed with methylene chloride. The combined methylene chloride solutions were poured into ice-water, the resulting mixture was shaken vigorously and the organic layer was separated and washed with 125 ml. portions of the following solvents: water (1 fold), saturated $Na_2CO_3$ (2 fold), water (1 fold). After the usual drying and concentrating procedure, distillation of the residue gave 205 g. of trans-epoxyocimene (90% yield), b.p. 45°–47°/0.1 Torr. $d_4^{20} = 0.9082$; $n_D^{20} = 1.4802$.

The above epoxide has valuable odoriferous properties and is useful in the perfume industry.

b. 1. Conversion of trans-ocimene epoxide to trans-sec.-ocimenol 40 g. of trans-ocimene epoxide, prepared according to the description of paragraph a) above, was added to a solution of p-toluene sulphonic acid (8 g.) and hydroquinone (2 g.) in benzene (800 ml.) and the resulting mixture was stirred at 25°–30° for eight hours.

A 2% NaOH solution (160 ml.) was added and the whole mixture was stirred vigorously for one hour. The organic layer was separated and washed twice with water. It was dried over $Na_2SO_4$, concentrated under vacuum and distilled over 2 g. of solid $Na_2CO_3$.

25 g. (60%) of pure trans-sec.-ocimenol, 2,6-dimethyl-2,5,7-octatrien-3-ol, b.p. 45°–47°/0.001 Torr, were thus obtained. $n_D^{20} = 1.4983$; $d_4^{20} = 0.9083$.

b. 2. Conversion of trans-ocimene epoxide to trans-sec.-ocimenol

To 500 ml. of 50% aqueous sulphuric acid acid cooled between −5° and 0° were added dropwise 75 g. of transepoxyocimene prepared according to the description of paragraph a) above. The mixture was vigorously stirred for one hour while the temperature was allowed to slowly rise to 20°–25°. It was extracted with methylene chloride, the extract was washed several times with water, with a saturated aqueous solution of sodium carbonate and finally with water. The extract was dried, concentrated and distilled. Thus secondary trans-ocimenol was obtained with a yield of 70–80%.

c. Reaction of trans-sec.-ocimenol with vinyl ethyl ether

A mixture containing 50 g. of trans-sec.-ocimenol, prepared according to the descriptions of paragraphs b) 1. or b) 2. above, 300 g. of ethyl vinyl ether, 5 g. of mercuric acetate, 10 g. of sodium acetate was refluxed for 40 hours under nitrogen. After cooling, the liquid was filtered and washed with 300 ml. of water. The excess vinyl ether was evaporated and the residue was diluted with 200 ml. of xylene. This solution was heated for one hour at 150°, then the xylene was removed under vacuum. The residue was distilled and yielded 35 g. (60%) of trans-4-methyl-8-vinyl-4,7-nonadienal, b.p. 40°–60°/0.04 Torr. According to the chromatographic analysis this product contained approximately 30% of sec.-ocimenol which caused no trouble when the aldehyde was converted to α-sinensal and which was recovered at this last stage.

The above aldehyde has valuable odoriferous properties and is useful in the perfume industry.

d. α-Sinensal 350 mg. of lithium metal cut into small bits were suspended under nitrogen in 12 ml. of dry ether. The suspension was cooled to −20° and a solution containing 3.84 g. of methyl iodide (27 millimoles) in 8 ml. of ether was added dropwise. The temperature was allowed to rise to 0° and stirring was continued for an hour after which a solution of 2.13 g. of diisopropylamine (21 millimoles) in 20 ml. of ether was added dropwise at 0°. The mixture was stirred for 45 min. at 0°, then 2.83 g. of propylidene-(tert.)butylimine (25 millimoles) diluted with 10 ml. of ether were added over a period of 20 min. and finally, after an additional 20 min. of stirring at 0°, a solution containing 3.71 g. of trans-4-methyl-8-vinyl-4,7-nonadienal (21 millimoles), prepared according to the description of paragraph c) above in 10 ml. of ether was added dropwise within 20 min. at −60°. The temperature was allowed to rise to room temperature, while stirring was continued for an additional hour. The whole mixture was poured into a solution of 10 g. of oxalic acid and 150 ml of ice-water and, after 30 min. of stirring, the organic layer was separated and the aqueous layer extracted with ether. After washing and drying the combined extracts as usual, they were subjected to a fractional distillation, and 2.73 g. of α-sinensal, b.p. 115°–120°/0.1 Torr (60%) were collected. IR spectrum ($CHCl_3$): 1725, 1650, 1610, 995, 895 cm$^{-1}$; NMR($CCl_4$): 9.65 ppm (1 H, s), 6.35 ppm (1 H, t, J = 6 cps), 6.29 ppm (1 H, $d$ of $d$, J = 10 and 10 cps), 4.85 ppm (4 H), 2.83 ppm (2 H, $t$, J = 7 cps), 1.9 – 2.6 ppm (4 H), 1.72 ppm (9 H).

Example 2

Preparation of α-sinensal a. Iodo-4-methyl-3,5-hexadiene

A solution of 25.6 g. (146 mM) of bromo-4-methyl-3,5-hexadiene (mixture of cis-(30%) and trans-(70%) isomers) prepared according to Bull. Soc. Chim. France, 1964, 2533) and 25.5 g. (170 mM) of sodium iodide in 200 ml. of acetone was stirred and refluxed for 3 hours. After removal of most of the solvent in vacuo the mixture was diluted with water and extracted twice with pentane. The organic layers were washed with 5% sodium thiosulphate and water, then dried over sodium sulphate and evaporated. Distillation of the residue afforded 27.5 g. (85%) of iodide, b.p. 40°–43°/0.02 Torr. IR($CHCl_3$): 1810, 1640, 1610, 990, 910 cm$^{-1}$. NMR($CCl_4$): 1.70 ppm (70%) / 1.78 ppm (30%)(2t, J = about 1 cps, 3 H); 2.5 – 3.3 ppm (m, 4 H); 4.8 – 5.5 ppm (m, 3 H) and 6.29 ppm (70%) / 6.62 ppm (30%) (2d of d, J = 10 and 17 cps, 1 H).

| Analysis: | | | |
|---|---|---|---|
| $C_7H_{11}I$ | C calculated 37.86 | found | 37.68% |
| | H calculated 4.99 | found | 5.00% |
| | I calculated 57.15 | found | 57.33% | b. 4-Methyl-3,5-hexadienyl triphenylphosphonium iodide

A mixture of 89.0 g. (0.40 mole) of iodo-4-methyl-3,5-hexadiene, 150 g. (0.40 mole) of triphenylphosphine and 350 ml. of benzene was stirred and refluxed for 8 hours. The solvent was removed in vacuo. After addition of about 1 l. of ether the oily mixture was left for one day at 0°. The crystallized salt was suction filtered, finely grinded and washed with ether, then dried for 4 hours at 80°/0.01 Torr. Obtained: 140 g. of phosphonium iodide, m.p. 124°–128°.

The mother liquors were concentrated (57 g.), taken up in 100 ml of benzene and refluxed for 8 hours. Treatment as above gave another 36 g. of salt, m.p. 123°–129°. Yield: 91%. IR($CHCl_3$): 1610, 1590, 1000, 910 cm$^{-1}$. NMR($CDCl_3$): 1.52 (70%) / 1.63 (30%) (2 s broad, 3 H) ppm. When in the example described in the above paragraph the iodo-compound was replaced by the corresponding bromo-compound, the corresponding phosphonium bromide was obtained.

c. 4 methyl-8-vinyl-4,7-nonadienal diethylacetal

To a stirred suspension of 77.2 g. (160 mM) of phosphonium iodide in 400 ml. of dry ether under nitrogen was added, at 0°, 10.2 g. (160 mM) of butyllithium (as a 20% solution in hexane). Stirring was continued for 45 min. at 0°, then 28.4 g. (164 mM) of levulinaldehyde diethylacetal (prepared according to Angew.

Chem. 64, 224 (1952)) in 100 ml. of ether was added over a period of 20 min. at 0°. After a night at room temperature the mixture was suction filtered and the salt washed with pentane. The filtrate was washed with water, dried over sodium sulphate and evaporated. Distillation of the residue gave, besides a forerun of recovered acetal, 14.1 g. (35%) of 4 methyl-8-vinyl-4,7-nonadienal diethylacetal, b.p. 104°–109°/0.1 Torr. IR(CHCl$_3$): 1640, 1610, 1160, 1060, 995, 905 cm$^{-1}$. NMR(CCl$_4$): 1.11 ppm ($t$, J = 7 cps, 6 H), 1.5 – 2.2 ppm ($m$, 10 H), 2.76 ($t$, J = 7 cps, 2 H), 3.2 – 3.7 ppm ($m$, 4 H), 4.30 ppm ($t$, J = 5 cps, 1 H), 4.7 – 5.4 ppm ($m$, 4 H), 6.20 ppm (75%) / 6.67 (25%) (2 $d$ of $d$, J = 11 and 17 cps, 1 H).

| Analysis: | | |
|---|---|---|
| C$_{16}$H$_{28}$O$_2$ | C calculated 76.14 | found 75.70% |
| | H calculated 11.18 | found 10.81% |

The above aldehyde has valuable odoriferous properties and is useful in the perfume industry.

d. 4-methyl-8-vinyl-4,7-nonadienal

A solution of 13.4 g. (53 mM) of the C$_{12}$-aldehyde diethylacetal, prepared according to the method described in paragraph c), 250 ml. of tetrahydrofuran, 60 ml. of water and and 0.5 ml. of 72% perchloric acid was left for 20 hours at room temperature under nitrogen. Water was added and the mixture was extracted with pentane (3x). The organic layers were washed with 5% NaHCO$_3$ and water, dried over sodium sulphate and evaporated. The remaining oil was distilled to yield 9.2 g. (99%) of 4 methyl-8-vinyl-4,7-nonadienal, b.p. 73°–75°/0.3 Torr. IR(CHCl$_3$): 2720, 1720, 1640, 1605, 995, 905 cm$^{-1}$. NMR(CCl$_4$): 1.4 – 1.8 ppm ($m$, 6 H), 2.2 – 2.5 ppm ($m$, 4H), 2.78 ppm ($t$, J = 7 cps, 2 H), 4.6 – 5.5 ppm ($m$, 4 H), 6.20 ppm (about 75%) / 6.64 ppm (about 25%) (2 $d$ of $d$, J = 10 and 17 cps, 1 H), 9.55 ppm ($t$, J = about 1.5 cps, 1 H).

| Analysis: | | |
|---|---|---|
| C$_{12}$H$_{18}$O | C calculated 80.85 | found 80.88% |
| | H calculated 10.18 | found 10.18% |

The above aldehyde has valuable odoriferous properties and is useful in the perfume industry.

e. α-Sinensal

Dry ether (20 ml.) was placed in a 200 ml. three-necked flask fitted with a magnetic stirrer, a dropping funnel and a thermometer. The air was swept out of the flask with dry nitrogen and a steady flow was maintained throughout the reaction. Finely cut lithium wire (420 mg; 60 mg.-atoms) was introduced and the stirred suspension was cooled to −10°. A solution of 4.55 g. (32 mM) of methyl iodide in 10 ml. of ether was added in the course of 20 min. while the temperature was maintained at −20° to −10°. Stirring was continued for one hour at 0°. Diisopropylamine (3.05 g., 30 mM) (freshly distilled over NaH) was added at −10° over a period of 10 min. and stirring was continued at 0° until methane evolution had ceased (about 20 min.) Propylidene-tert.-butylimine (3.40 g.; 30 mM) was then added at −10° over a period of 15 min. and stirring was continued at 0° for 30 min. Finally, a solution of 4.45 g (25 mM) of 4-methyl-8-vinyl-4,7-nonadienal, prepared according to the description of paragraph d), in 10 ml. of ether was added at −60° within 20 min. After leaving overnight at room temperature the mixture was poured in an ice-cold solution of 10 g. of oxalic acid in 100 ml. of water. The mixture was stirred for 30 min. then it was extracted twice with pentane. The organic layers were washed with 5% NaHCO$_3$ and water, dried over sodium sulphate and evaporated. Distillation of the residue gave 3.87 g. (71%) of a α-sinensal, b.p. 115°–120°/0.1 Torr. This product contained about 10% of starting aldehyde. An analytical sample was obtained by redistillation over a small Vigreux-column, followed by chromatography on silicic acid using hexane + 3% AcOEt as eluent. It had b.p. 100°–102°/0.07 Torr.

| Analysis: | | |
|---|---|---|
| C$_{15}$H$_{22}$O | C calculated 82.51 | found 82.54% |
| | H calculated 10.16 | found 10.27% |

Example 3

Preparation of cis-ocimene epoxide

Cis-ocimene was epoxidised according to the method used for trans-ocimene described in Example 1 a). Cis-ocimene epoxide gave the following constants: $d_4^{20}$ = 0.8996; $n_D^{20}$ = 1.4721 and was obtained with about 90% yield.

The above epoxide has valuable odoriferous properties and is useful in the perfume industry.

When the above epoxide is used in the processes described in Example 1, the corresponding cis-sec.-ocimenol and the corresponding cis-C-12 aldehyde are obtained.

Example 4

Preparation of β-sinensal a. Epoxidation of myrcene

Freshly distilled commercial myrcene (204 g.) containing about 10% limonene was epoxidised according to the method for obtaining epoxy-ocimene described in Example 1 a).

Epoxymyrcene (205 g.), b.p. 41°–44°/0.06 Torr, was thus obtained with a 90% yield.

| Analysis: | | |
|---|---|---|
| C$_{10}$H$_{16}$O | C calculated 78.89% | found 78.65% |
| | H calculated 10.59% | found 10.40% |

$n_D^{20}$ = 1.4632; $d_4^{20}$ = 0.8865 $[\alpha]_D^{20}$ = −3.95°

The above epoxide has valuable odoriferous properties and is useful in the perfume industry.

b. 1. Conversion of myrcene epoxide to sec.-myrcenol

A solution containing 126.5 g. (1.25 moles) of diisopropylamine in 500 ml. of cyclohexane was cooled to −10°. With good stirring and under nitrogen protection there was added dropwise, over a period of 20 min., a solution of butyllithium (465 g. of a 15% solution in hexane = 1.25 moles). Stirring was continued for a further 10 min. at 0°, then it was cooled again to −5°, and 76 g. (0.5 mole) of epoxy-myrcene, prepared according to the method described in paragraph a) were added dropwise during 10 min. After the addition, the temperature was allowed to slowly rise to 25°, which temperature was maintained for 1½ hour. The reaction mixture was poured into ice-water, then the organic layer was separated, washed (first with aqueous 10% HCl, then with water) and dried. Each washing fraction was extracted with petroleum ether (250 ml.), the various extracts were combined, concentrated and distilled. 53 g. (69.8%) of sec.-myrcenol, b.p. 47°/0.04 Torr, were obtained.

| Analysis: | | |
|---|---|---|
| $C_{10}H_{16}O$ | C calculated 78.89 | found 78.61% |
| | H calculated 10.59 | found 10.37% |

$n_D^{20} = 1.4890$; $d_4^{20} = 0.8996$; $[\alpha]_D^{20} = -1.8°$ b. 2. Conversion of myrcene epoxide to sec.-myrcenol To 465 g. of a solution of about 15% of butyllithium in hexane was added dropwise, under nitrogen at a temperature of −10°, a solution of 126.5 g. of diisopropylamine in 500 ml. of cyclohexane.

76 g. of epoxymyrcene, prepared according to the method described in paragraph a) by epoxidation of myrcene, were added dropwise between −5° and 0°, with good stirring. Then the mixture was stirred with 200 ml. ice-water and neutralised with diluted HCl. Following the same isolation procedure described in paragraph b) 1. the sec.-myrcenol was obtained with a comparable yield.

c. 4-methyl-8-vinyl-4,8-nonadienal

A mixture of 50 g. of sec.-myrcenol (prepared according to the method described in paragraph b) above), 300 g. of n-butyl vinyl ether, 1 g. of mercuric acetate and 10 g. of sodium acetate were refluxed for 40 hours (120°) under nitrogen. During this heating period 1 g. of additional mercuric acetate was added every 6 hours. The laboratory vessel was connected to a downward directed condenser, and the excess of n-butyl vinyl ether was distilled under ordinary pressure. The residue was distilled under vacuum. A yield of 75% of 4-methyl-8-vinyl-4,8-nonadienal that contained approximately 15% of unreacted alcohol was obtained. This alcohol could be recovered when the above $C_{12}$ aldehyde was converted to $\beta$-sinensal.

d. $\beta$-Sinensal

A solution containing 600 ml. of absolute ether and 640 g. (1.5 moles) of butyl lithium in the form of a 15% solution in hexane was cooled to −10°. In the course of one hour, a solution of 128 g. of diisopropylamine (1.265 moles) in 600 ml. of absolute ether was added with stirring and under nitrogen, then the temperature was allowed to rise to 0°, and stirring was continued for an additional ½ hour. The solution was again cooled to −10° and a solution containing 208 g. of propylidenecyclohexylimine (1.5 moles, b.p. 56°–58°/15 Torr) in 600 ml. of ether was added dropwise over a period of one hour. The mixture was stirred for one hour at 0°, then cooled to −65°, there was then added thereto, within a period of ½ hour, 225 g. of 4-methyl-8-vinyl-4,8-nonadienal (1.265 moles) dissolved in 600 ml. of ether, while maintaining the temperature between −66° and −62°. The temperature was allowed to come back to 25° in the course of one hour. The reaction mixture was then poured into 8.1 of water at 0° that contained 600 g. of oxalic acid, under stirring. The organic layer was separated and the aqueous phase extracted twice with ether ( 2 l.). The extracts were washed with aqueous 5% bicarbonate and with water. After drying and evaporation a yield of 70% of crude $\beta$-sinensal was obtained. B.p. 100°–111°/0.04 Torr. An analytical sample was prepared by chromatography on silica with a 3% solution of ethyl acetate in hexane (v/v) as the eluent; b.p. 88°–89°/0.02 Torr. Spectral measurements; IR ($CHCl_3$): 3090, 2710, 1800, 1680, 1640, 1590, 995, 905 cm$^{-1}$, UV (EtOH): 2260 A ($\epsilon$= 34,000). NMR ($CCl_4$): 9.33 ppm (1 H, s), 6.37 ppm (1 H, t, J = 6 cps), 6.30 ppm (1 H, d of d, J = 17 and 10 cps), 4.8 − 5.4 ppm (5 H, m), 1.9 − 2.6 ppm (8 H, m), 1.69 ppm (3 H, s broad), 1.61 ppm (3 H, s broad).

| Analysis: | | |
|---|---|---|
| $C_{15}H_{22}O$ | C calculated 82.51% | found 82.58% |
| | H calculated 10.16% | found 10.39% |

The dinitrophenylhydrazone of $\beta$-sinensal melted at 86°–88.5°C.

Example 5

Preparation of $\beta$-sinensal a. Preparation of myrcenyl bromide

A solution containing 52.4 g. (345 millimoles) of myrcenol (prepared from myrcene according to Bull. Soc. Chim. 5, 931 (1938)), 8.5 g. (105 millimoles) of anhydrous pyridine and 200 ml. of anhydrous hexane was prepared. 40.5 g. (105 millimoles) of phosphorus tribromide diluted with 30 ml. of hexane were added dropwise to this solution with stirring at −10°C. Stirring was continued for 30 min. at 0° C., and then 200 g. of ice were added portionwise. After further stirring for 30 min. at room temperature, the organic layer was separated and washed with water, with a 5% $NaHCO_3$ solution and again with water. After drying over $Na_2SO_4$ the extract was subjected to distillation to obtain 43.2 g. of myrcenyl bromide, b.p. 61°–64°C./0.03 Torr; yield 58%. The spectrographic measurements gave the following results: IR ($CHCl_3$): 3080, 1800, 1660, 1630, 1590, 990, 905 cm$^{-1}$, NMR ($CCl_4$): 6.33 ppm (1 H, d of d, J = 17 and 11 cps), 4.8 − 5.7 ppm (5 H, m), 3.91 ppm (2 H, s), 2.2 ppm (4 H, m), 1.74 ppm (3 H, s).

b. Preparation of 4-methyl-8-vinyl-4,8-nonadien-1-al

A suspension of 770 mg. of lithium cut into small pieces in 20 ml. of anhydrous ether was prepared under nitrogen protection. The suspension was cooled and maintained between −10° and −20° C. and there was added thereto, within a period of 30 min., a solution of 8.23 g. (58 millimoles) of methyl iodide in 15 ml. of ether. After stirring this mixture at 0° for one hour, there were added dropwise, within a period of 20 min., 5.56 g. (55 millimoles) of diisopropylamine (freshly distilled over sodium hydride) diluted with 10 ml. of ether, while maintaining the temperature below or at 10°. Stirring was continued for about 45 min. at 0°, during which time an evolution of gas was observed. When the evolution of gas ended there was added at −10° over a period of 15 min. a solution of 7.5 g. (75 millimoles) of ethylidene-tert.-butylimine in 5 ml. of ether and then, after 20 min. of stirring at 10°, a solution of 10.7 g. (50 millimoles) of myrcenyl bromide, prepared according to the method described in paragraph a), in 5 ml. of ether over a period of 15 min. at −20°. Stirring was continued overnight at room temperature, whereupon the whole was poured into a solution, cooled to 0°, of 30 g. of oxalic acid in 400 ml. of water. Stirring was continued for 20 min., the organic layer was separated and the aqueous phase was twice extracted with ether. The ethereal extracts were washed with water, dried over $Na_2SO_4$ and distilled. There were obtained 7.84 g. of liquid, b.p. 65°–67°/0.03 Torr. The distilled product was subjected to chromatography on a column containing 200 g. of silicic acid and, as an eluent, 725 ml. of hexane containing 3% of ethyl acetate (v/v).

The tail fraction of the eluate, 450 ml., yielded after evaporation of the solvent 5.46 g. (61%) of 90% pure 4-methyl-8-vinyl-4,8-nonadien-1-al as shown by gas-chromatographic analysis; b.p. 60°/0.02 Torr. Spectrographic measurements: IR (CHCl$_3$): 3080, 2720, 1790, 1720, 1630, 1590, 990, 905 cm$^{-1}$. UV (ethanol): 2240 A ($\in$ = 18,600). NMR (CCl$_4$): 9.73 ppm (1 H, $t$, J = 1.5 cps), 6.35 ppm (1 H, $d$ of $d$, J = 17 and 10 cps), 4.8 – 5.5 ppm ( 5 H, $m$), 2.0 – 2.7 ppm (8 H, $m$), 1.61 ppm (3 H, $s$ broad).

| Analysis: | | |
|---|---|---|
| C$_{12}$H$_{18}$O | C calculated 80.85 | found 80.84% |
| | H calculated 10.18 | found 10.44 | c. β-Sinensal

4-Methyl-8-vinyl-4,8-nonadienal was used in place of 4-methyl-8-vinyl-4,7-nonadienal in the reaction described in Example 1 $d$). for preparing α-sinensal. The resulting aldehyde, β-sinensal, was obtained in comparable yields and had the same constants as the product obtained according to Example 4 $d$).

Example 6

Isomerisation of β-sinensal to α-sinensal

A mixture of 1 g. of β-sinensal and 250 mg. of a carbon-palladium catalyst previously activated with hydrogen was stirred overnight at 70°. The solution was filtered, concentrated and subjected to fractional distillation. 0.6 g. of α-sinensal was collected. B.p. 95°–100°/0.002 Torr, identical with natural α-sinensal.

The following Example illustrates the use of transepoxy-ocimene as a modifying and enhancing agent in the preparation of perfumes.

Example 7

A lavender perfume composition was prepared by mixing the following ingredients (parts by weight):

| Ingredients | Parts by weight |
|---|---|
| Lavender oil | 510 |
| Rosemary oil | 20 |
| Clary sage oil | 30 |
| Bergamot oil | 90 |
| Lemon oil | 40 |
| Geranium Bourbon | 40 |
| Nonanal at 1%* | 10 |
| Undecanal at 1%* | 20 |
| Dodecanal at 1%* | 10 |
| Methylphenyl ketone at 10%* | 5 |
| Phenylethyl alcohol | 40 |
| Citronellyl acetate | 10 |
| Coumarin | 50 |
| Musk ambrette | 10 |
| Musk ketone | 30 |
| Lavender absolute | 40 |
| Oak moss absolute | 5 |
| Pentadecanolide | 25 |
| | 985 |

*in diethyl phthalate

When 15 g. of trans-epoxy-ocimene were added to 985 g. of the above composition, the top note were markedly improved and more natural.

The following Example illustrates the use of aldehydes II$a$ and II$b$ as fragrances in perfume compositions.

Example 8

A perfume composition having an aldehydic floral odour was prepared by mixing the following ingredients:

| Ingredients | Parts by weight |
|---|---|
| Nonanal at 10%* | 15 |
| Decanal at 10%* | 5 |
| Undecanal at 10%* | 15 |
| Dodecanal at 10%* | 5 |
| Phenylethylalcohol | 150 |
| Citronellol | 90 |
| Geraniol | 60 |
| Linalool | 15 |
| Linalyl acetate | 60 |
| Benzyl acetate | 120 |
| p-tert.-Butyl-cyclohexyl acetate | 30 |
| Hydroxycitronellal | 60 |
| Amylcinnamic aldehyde | 20 |
| Isomethyl-γ-ionone | 120 |
| Ylang Ylang | 25 |
| Coumarin | 30 |
| Neroli bigarade | 5 |
| Musk Ambrette | 10 |
| Musk Ketone | 20 |
| Geranium (terpeneless) at 10%* | 30 |
| Undecanolide at 1%* | 30 |
| Diethyl phthalate | 70 |
| | 985 |

*in diethyl phthalate

By adding 15 parts by weight of aldehyde II$b$ to this perfume composition the top odour thereof was substantially reinforced. Similar results were obtained by adding the same quantity of aldehyde II$a$.

What we claim is:

1. As a new composition of matter, a nonadienal selected from the group consisting of 4-methyl-8-vinyl-4,7-nonadienal and 4-methyl-8-vinyl-4,8-nonadienal.

2. A new composition of matter according to claim 1 in which the nonadienal is 4-methyl-8-vinyl-4,7-nonadienal.

3. A new composition of matter according to claim 1 in which the nonadienal is 4-methyl-8-vinyl-4,8-nonadienal.

* * * * *

UNITED STATES PATENT AND TRADEMARK OFFICE
CERTIFICATE OF CORRECTION

PATENT NO. : 3,963,783
DATED : June 15, 1976
INVENTOR(S) : George Hermann Buchi, et al.

It is certified that error appears in the above–identified patent and that said Letters Patent are hereby corrected as shown below:

Column 1, line 45 "mmixed" should be --mixed--

Column 4, lines 3-4 "e.g. toluene or chlorobenzene" should be --e.g. benzene, toluene or chlorobenzene--

Column 8, line 47 "150 g." should be --105 g.--

Column 11, line 8 "0.8996" should be --0.8986--

Column 11, line 67 "2260 A" should be --2260 Å--

Column 13, line 7 "2240 A" should be --2240 Å--

Signed and Sealed this

Sixth Day of November 1979

[SEAL]

Attest:

RUTH C. MASON
Attesting Officer

LUTRELLE F. PARKER
Acting Commissioner of Patents and Trademarks